(12) United States Patent
Larelle et al.

(10) Patent No.: US 8,153,556 B2
(45) Date of Patent: Apr. 10, 2012

(54) SYNERGISTIC HERBICIDAL COMPOSITIONS CONTAINING BENFLURALIN

(75) Inventors: Dominique Larelle, Le Tremblay sur Mauldre (FR); Jean-Louis Cardon, Saint Quentin en Yvelines (FR); Richard K. Mann, Franklin, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 12/969,966

(22) Filed: Dec. 16, 2010

(65) Prior Publication Data

US 2011/0152098 A1    Jun. 23, 2011

Related U.S. Application Data

(60) Provisional application No. 61/287,823, filed on Dec. 18, 2009.

(51) Int. Cl.
*A01N 25/26* (2006.01)
*A01N 43/40* (2006.01)
*A01N 43/00* (2006.01)
*A01N 33/18* (2006.01)

(52) U.S. Cl. ......... 504/100; 504/130; 504/139; 504/347
(58) Field of Classification Search ................. None
See application file for complete search history.

*Primary Examiner* — Alton Pryor
(74) *Attorney, Agent, or Firm* — Craig E. Mixan

(57) ABSTRACT

An herbicidal composition containing (a) benfluralin and (b) either diflufenican, flufenacet or prosulfocarb provides synergistic control of selected weeds in cereals.

7 Claims, No Drawings

SYNERGISTIC HERBICIDAL COMPOSITIONS CONTAINING BENFLURALIN

This application claims the benefit of U.S. Provisional Application Ser. No. 61/287,823 filed on 18 Dec. 2009. This invention concerns a synergistic herbicidal composition containing (a) benfluralin and (b) an herbicide selected from the group of diflufenican, flufenacet and prosulfocarb.

FIELD OF THE INVENTION

Background of the Invention

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, herbicidal active ingredients have been shown to be more effective in combination than when applied individually and this is referred to as "synergism." As described in the *Herbicide Handbook* of the Weed Science Society of America, Eighth Edition, 2002, p. 462, "'synergism' [is] an interaction of two or more factors such that the effect when combined is greater than the predicted effect based on the response to each factor applied separately." The present invention is based on the discovery that (a) benfluralin and (b) an herbicide selected from the group of diflufenican, flufenacet and prosulfocarb, already known individually for their herbicidal efficacy, display a synergistic effect when applied in combination.

The herbicidal compounds forming the synergistic composition of this invention are independently known in the art for their effects on plant growth.

Benfluralin, N-butyl-N-ethyl-2,6-dinitro-4-(trifluoromethyl)benzenamine, is a dinitroaniline herbicide that is also referred to as benefin or bethrodine. It is described in *The Pesticide Manual*, Fourteenth Edition, 2006. Benfluralin is applied pre-emergence or pre-plant incorporated to control annual grasses and broadleaf weeds in a variety of crops.

Diflufenican, N-(2,4-difluorophenyl)-2-[3-(trifluoromethyl)phenoxy]-3-pyridinecarboxamide, is a pyridinecarboxamide herbicide that is also referred to as diflufenicanil. It is described in *The Pesticide Manual*, Fourteenth Edition, 2006. Diflufenican is applied pre- or early post-emergence to control grass and broadleaf weeds in wheat and barley.

Flufenacet, N-(4-fluorophenyl)-N-(1-methylethyl)-2-[[5-(trifluoromethyl)-1,3,4-thiadiazol-2-yl]oxy]acetamide, is an oxyacetamide herbicide. It is described in *The Pesticide Manual*, Fourteenth Edition, 2006. Flufenacet is applied pre-emergence or pre-plant incorporated to control grass and some broadleaf weeds in a variety of crops.

Prosulfocarb, S-(phenylmethyl) dipropylcarbamothioate, is a thiocarbamate herbicide. It is described in *The Pesticide Manual*, Fourteenth Edition, 2006. Prosulfocarb is applied pre- or early post-emergence to control a wide range of grass and broadleaf weeds in wheat, barley and rye.

SUMMARY OF THE INVENTION

The present invention concerns a synergistic herbicidal mixture comprising an herbicidally effective amount of (a) benfluralin and (b) an herbicide selected from the group of diflufenican, flufenacet and prosulfocarb. The compositions may also contain an agriculturally acceptable adjuvant or carrier.

The present invention also concerns a method of controlling the growth of undesirable vegetation, particularly in cereals, and the use of this synergistic composition.

The species spectrum of the compounds of the synergistic mixture, i.e., the weed species which the respective compounds control, is broad and highly complementary. These synergistic mixtures are particularly useful for the control of key weeds, e.g., blackgrass (*Alopecurus agrestis* L., ALOMY), round-leaved Cranesbill (*Geranium rotundifolium* L., GERRT), cleavers (*Galium aparine* L., GALAP) and ivyleaf speedwell (*Veronica hederifolia* L., VERHE), in cereal crops.

DETAILED DESCRIPTION OF THE INVENTION

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the synergistic mixture when they are applied to the seed or locus of the plant before planting or emergence. The effect observed depends upon the plant species to be controlled, the application parameters of dilution, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the composition of the present invention pre-emergence, prior to the emergence of the weeds with or without mechanical soil incorporation to achieve the maximum control of weeds.

In the composition of this invention, the weight ratio of benfluralin to the other herbicide component at which the herbicidal effect is synergistic lies within the range of between about 30:1 and about 1:3. Preferably the weight ratio of benfluralin to the other herbicide component lies within the range of between about 12:1 and about 1:3.

The rate at which the synergistic composition is applied will depend upon the soil type, the particular type of weed to be controlled, the degree of control required, the length of weed control and the timing and method of application. In general, the composition of the invention can be applied at an application rate of between about 0.5 kilograms per hectare (kg/ha) and about 6.5 kg/ha based on the total amount of active ingredients in the composition. An application rate between about 1.0 kg/ha and about 4.0 kg/ha is preferred. In especially preferred embodiments of the invention, benfluralin is applied at a rate between about 0.5 kg/ha and about 1.5 kg/ha and diflufenican is applied at a rate between about 0.03 kg/ha and about 0.15 kg/ha, flufenacet is applied at a rate between about 0.1 kg/ha and about 0.3 kg/ha and prosulfocarb is applied at a rate between about 1.0 kg/ha and about 4.0 kg/ha.

The components of the synergistic mixture of the present invention can be applied either separately or as part of a multipart herbicidal system.

The synergistic mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the synergistic composition of the present invention include: 2,4-D, amidosulfuron, beflubutamid, bifenox, bromoxynil, carfentrazone-ethyl, chlormequat, chlortoluron, cinidon-ethyl, clodinafop-propargyl, clopyralid, cyanazine, dicamba, diclofop-methyl, dimefuron, fenoxaprop, fenoxaprop-ethyl, fenoxaprop-ethyl+isoxadifen-ethyl, fenoxaprop-p-ethyl, florasulam, flucarbazone, flumetsulam, flupyrsulfuron, fluoroxypyr, flurtamone, glyphosate, glufosinate, imazamethabenz, imazamox, imazapic, imazapyr, imazaquin, imazethapyr, imazosulfuron, indanofan, iodosulfuron, iodosulfuron-ethyl-sodium, ioxynil, isoproturon, isoxaben, KIH-845, lactofen, linuron, MCPA, mecoprop-P, mesosulfuron, mesosulfuron-ethyl sodium, metosulam, metribuzin, metsulfuron, metsulfuron-methyl, oxyfluorfen, paraquat, pendimethalin, penoxsulam, picolinafen, pinoxaden, propoxycarbazone, prosulfuron, pyraflufen-ethyl, pyribenzoxim (LGC-40863), pyroxsulam, saflufenacil, sulfosate, sulfosulfuron, thifensulfuron, thifensulfuron-methyl, topramezone, tralkoxydim, triasulfuron, tribenuron and tribenuron-methyl.

The compounds of the present invention can additionally be employed to control undesirable vegetation in many crops that have been made tolerant to or resistant to them or to other herbicides by genetic manipulation or by mutation and selection. The herbicidal compounds of the present invention can, further, be used in conjunction with glyphosate, glufosinate, dicamba, imidazolinones or 2,4-D on glyphosate-tolerant, glufosinate-tolerant, dicamba-tolerant, imidazolinone-tolerant or 2,4-D-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix. Similarly the herbicidal compounds of the present invention can be used in conjunction with acetolactate synthase inhibitors on acetolactate synthase inhibitor tolerant crops.

The synergistic composition of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyr-diethyl, MG 191, MON 4660, naphthalic anhydride (NA), oxabetrinil, R29148 and N-phenylsulfonylbenzoic acid amides, to enhance their selectivity.

While it is possible to utilize the synergistic mixtures of the present invention directly as herbicides, it is preferable to use them in mixtures containing a herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of the synergistic mixture or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alfa, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate;

soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulators, fungicides, insecticides, and the like, and can be formulated with liquid fertilizers or solid, particulate fertilizer carriers such as ammonium nitrate, urea and the like.

The concentration of the active ingredients in the synergistic composition of the present invention is generally from 0.001 to 98 percent by weight. Concentrations from 10 to 90 percent by weight are often employed. In compositions designed to be employed as concentrates, the active ingredients are generally present in a concentration from 5 to 98 weight percent, preferably 10 to 90 weight percent. Such compositions are typically diluted with an inert carrier, such as water, before application. The diluted compositions usually applied to weeds or the locus of weeds generally contain 0.0001 to 1 weight percent active ingredient and preferably contain 0.001 to 0.1 weight percent.

The present compositions can be applied to weeds or their locus by the use of conventional ground or aerial dusters, sprayers, and granule applicators, by addition to irrigation water, and by other conventional means known to those skilled in the art.

EXAMPLES

Evaluation of Benefin Tank Mixes for Synergistic Weed Control in Winter Wheat in France and Germany Soft winter wheat was planted using normal cultural practices in France and Germany in October under normal environmental conditions that allowed rapid germination and growth of wheat and weeds. Fields were prepared as per normal cultural practices, by applying appropriate fertilizers for normal winter wheat growth and yield, working and leveling the ground, and planting at normal time of year using 150 to 170 kg/ha seed with mechanical planters to maximize emergence, growth and yield. Weed infestations varied from 280 to 500 plants per square meter (plants/m$^2$).

Treatments consisted of benfluralin applied alone, as well as diflufenican, flufenacet and prosulfocarb applied alone, and in combination with benfluralin, to measure herbicidal weed control and any synergistic interactions. These treatments were applied using backpack sprayers applying spray volumes of 200-250 liters per hectare (L/ha) at a spray pressure of 230 KPA to plots 2.5 meters (m)×8 m, randomized 4 times per treatment. All treatments were applied pre-emergence to the soil, after planting the winter wheat. The pre-emergence treatments were activated with normal rainfall. Treatments were rated on a 0-100% scale, with 0%=no control and 100%=complete control.

Colby's equation was used to determine the herbicidal effects expected from the mixtures (Colby, S. R. *Weeds* 1967, 15, 20-22. Calculation of the synergistic and antagonistic response of herbicide combinations).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

The herbicide tankmix combinations tested, application rates and ratios employed, plant species tested, and results are given in Tables 1 to 6. Tables 1 and 2 demonstrate synergy results for benfluralin+diflufenican in 2 separate trials, Tables 3 and 4 demonstrate synergy results for benfluralin+flufenacet in 2 separate trials, and Tables 5 and 6 demonstrate synergy results for benfluralin+prosulfocarb in 2 separate trials.

TABLE 1

Test 1 - Benfluralin + Diflufenican Synergy Results

| Application Rate (g ai/ha) | | Days After Application | % Visual Weed Control | | | |
|---|---|---|---|---|---|---|
| | | | ALOMY | | GERRT | |
| Benfluralin | Diflufenican | | Obs | Exp | Obs | Exp |
| 1,000 | 0 | 27 | 17 | — | 6 | — |
| 0 | 100 | 27 | 19 | — | 72 | — |
| 1,000 | 100 | 27 | 47 | 34 | 81 | 74 |
| 1,000 | 0 | 174 | 20 | — | — | — |
| 0 | 100 | 174 | 22 | — | — | — |
| 1,000 | 100 | 174 | 52 | 37 | — | — |
| 1,000 | 0 | 236 | 23 | — | 7 | — |
| 0 | 100 | 236 | 23 | — | 63 | — |
| 1,000 | 100 | 236 | 62 | 41 | 91 | 65 |

ALOMY = *Alopecurus agrestis* L. (blackgrass)
GERRT = *Geranium rotundifolium* L. (round-leaved Cranesbill)
Obs = observed values
Exp = expected, calculated values
g ai/ha = gram active ingredient per hectare

TABLE 2

Test 2- Benfluralin + Diflufenican Synergy Results

| Application Rate (g ai/ha) | | Days After Application | % Visual Weed Control ALOMY | |
|---|---|---|---|---|
| Benfluralin | Diflufenican | | Obs | Exp |
| 1,000 | 0 | 169 | 0 | — |
| 0 | 100 | 169 | 0 | — |
| 1,000 | 100 | 169 | 33 | 0 |
| 1,000 | 0 | 199 | 0 | — |
| 0 | 100 | 199 | 7 | — |
| 1,000 | 100 | 199 | 43 | 7 |

ALOMY = *Alopecurus agrestis* L. (blackgrass)
Obs = observed values
Exp = expected, calculated values
g ai/ha = gram active ingredient per hectare

TABLE 3

Test 1 - Benfluralin + Flufenacet Synergy Results

| Application Rate (g ai/ha) | | Days After Application | % Visual Weed Control ALOMY | |
|---|---|---|---|---|
| Benfluralin | Flufenacet | | Obs | Exp |
| 1,200 | 0 | 13 | 7 | — |
| 0 | 240 | 13 | 26 | — |
| 1,200 | 240 | 13 | 52 | 31 |
| 1,200 | 0 | 236 | 29 | — |
| 0 | 240 | 236 | 80 | — |
| 1,200 | 240 | 236 | 93 | 85 |

ALOMY = *Alopecurus agrestis* L. (blackgrass)
Obs = observed values
Exp = expected, calculated values
g ai/ha = gram active ingredient per hectare

TABLE 4

Test 2 - Benfluralin + Flufenacet Synergy Results

| Application Rate (g ai/ha) | | Days After Application | % Visual Weed Control ALOMY | | VERHE | |
|---|---|---|---|---|---|---|
| Benfluralin | Flufenacet | | Obs | Exp | Obs | Exp |
| 1,200 | 0 | 150 | — | — | 43 | — |
| 0 | 240 | 150 | — | — | 0 | — |
| 1,200 | 240 | 150 | — | — | 62 | 43 |
| 1,200 | 0 | 189 | 0 | — | — | — |
| 0 | 240 | 189 | 82 | — | — | — |
| 1,200 | 240 | 189 | 97 | 82 | — | — |

ALOMY = *Alopecurus agrestis* L. (blackgrass)
VERHE = *Veronica hederifolia* L. (ivyleaf speedwell)
Obs = observed values
Exp = expected, calculated values
g ai/ha = gram active ingredient per hectare

TABLE 5

Test 1 - Benfluralin + Prosulfocarb Synergy Results

| Application Rate (g ai/ha) | | Days After Application | % Visual Weed Control | | | | | |
|---|---|---|---|---|---|---|---|---|
| | | | ALOMY | | GALAP | | GERRT | |
| Benfluralin | Prosulfocarb | | Obs | Exp | Obs | Exp | Obs | Exp |
| 1,000 | 0 | 27 | 17 | — | 7 | — | 6 | — |
| 0 | 3,000 | 27 | 30 | — | 37 | — | 21 | — |
| 1,000 | 3,000 | 27 | 63 | 42 | 68 | 42 | 33 | 25 |
| 1,000 | 0 | 174 | 20 | — | 8 | — | 7 | — |
| 0 | 3,000 | 174 | 33 | — | 39 | — | 25 | — |
| 1,000 | 3,000 | 174 | 70 | 47 | 72 | 44 | 38 | 30 |
| 1,000 | 0 | 236 | 23 | — | 7 | — | 7 | — |
| 0 | 3,000 | 236 | 35 | — | 42 | — | 27 | — |
| 1,000 | 3,000 | 236 | 94 | 50 | 78 | 47 | 42 | 32 |

ALOMY = *Alopecurus agrestis* L. (blackgrass)
GALAP = *Galium aparine* L. (cleavers)
GERRT = *Geranium rotundifolium* L. (round-leaved Cranesbill)
Obs = observed values
Exp = expected, calculated values
g ai/ha = gram active ingredient per hectare

TABLE 6

Test 2- Benfluralin + Prosulfocarb Synergy Results

| Application Rate (g ai/ha) | | Days After Application | % Visual Weed Control ALOMY | |
|---|---|---|---|---|
| Benfluralin | Prosulfocarb | | Obs | Exp |
| 1,000 | 0 | 189 | 0 | — |
| 0 | 3,000 | 189 | 30 | — |
| 1,000 | 3,000 | 189 | 52 | 30 |

ALOMY = *Alopecurus agrestis* L. (blackgrass)
Obs = observed values
Exp = expected, calculated values
g ai/ha = gram active ingredient per hectare Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A synergistic herbicidal mixture comprising an herbicidally effective amount of (a) benfluralin and (b) an herbicide selected from the group of diflufenican, flufenacet and prosulfocarb.

2. The mixture of claim 1 in which the selected herbicide is diflufenican.

3. The mixture of claim 1 in which the selected herbicide is flufenacet.

4. The mixture of claim 1 in which the selected herbicide is prosulfocarb.

5. An herbicidal composition comprising an herbicidally effective amount of the synergistic herbicidal mixture of claim 1 and an agriculturally acceptable adjuvant or carrier.

6. A method of controlling undesirable vegetation in crops which comprises contacting the seed, or locus of the crops before planting or emergence, or applying to soil to prevent growth and or emergence of the undesirable vegetation the herbicidally effective amount the synergistic herbicidal mixture of claim 1.

7. A method of controlling undesirable vegetation in cereals which comprises contacting the seed, or locus of cereal plant before planting or emergence, or applying to soil to prevent growth and or emergence of undesirable vegetation the herbicidally effective amount the synergistic herbicidal mixture of claim 1.

* * * * *